(12) United States Patent
Brandao Silva et al.

(10) Patent No.: US 12,269,072 B2
(45) Date of Patent: Apr. 8, 2025

(54) PERSONAL CARE DEVICE

(71) Applicant: KONINKLIJKE PHILIPS N.V., Eindhoven (NL)

(72) Inventors: Priscilla Brandao Silva, Eindhoven (NL); Lutz Christian Gerhardt, Eindhoven (NL); Mark Thomas Johnson, Arendonk (BE); Bart Gottenbos, Budel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 19 days.

(21) Appl. No.: 18/269,197

(22) PCT Filed: Nov. 19, 2021

(86) PCT No.: PCT/EP2021/082361
§ 371 (c)(1),
(2) Date: Jun. 22, 2023

(87) PCT Pub. No.: WO2022/135806
PCT Pub. Date: Jun. 30, 2022

(65) Prior Publication Data
US 2024/0042498 A1    Feb. 8, 2024

(30) Foreign Application Priority Data
Dec. 22, 2020    (EP) .................................... 20216418

(51) Int. Cl.
*B08B 7/04*    (2006.01)
*A46B 15/00*   (2006.01)
(Continued)

(52) U.S. Cl.
CPC ........ *B08B 7/0035* (2013.01); *A46B 15/0004* (2013.01); *A46B 15/001* (2013.01);
(Continued)

(58) Field of Classification Search
CPC .............. A46B 15/0004; A46B 15/001; A46B 15/0012; A46B 15/0034; A46B 15/0036;
(Continued)

(56) References Cited

U.S. PATENT DOCUMENTS 9,585,687 B2   3/2017   Tenenbaum et al.
10,201,701 B2  2/2019   Levi
(Continued)

FOREIGN PATENT DOCUMENTS

EP    3747308 A1   12/2020
GB    2117230 A    10/1983
(Continued)

OTHER PUBLICATIONS

International Search Report and Written Opinion Dated Feb. 23, 2022 For International Application No. PCT/EP2021/082361 filed Nov. 19, 2021.
(Continued)

*Primary Examiner* — Randall E Chin

(57) ABSTRACT

A personal care device (12) comprising an RF signal generator (32) for generating RF-frequency electromagnetic emissions for a cleaning or treatment function. The RF emissions may be output from a set of two or more RF electrodes (22) (e.g. electrodes) upon stimulation with an RF drive signal in a frequency range from 3 kHz to 30 GHz from an RF signal generator. The device further includes a controller (34) for detect a degraded functional state of the RF electrodes (22) via monitoring changes or variations in one or more electrical characteristics of the RF signal generator (32), e.g. drift in one or more electrical characteristics from reference factory levels, or sudden changes in the characteristics, indicating a short-circuit. A response action can be generated based on the electrical characteristics meeting pre-defined criteria indicative of a certain degraded func-
(Continued)

tional status, for example generating a sensory alert for a user or data output, or performing remedial action such as deactivating sensed defective or worn electrodes.

14 Claims, 4 Drawing Sheets

(51) Int. Cl.
*B08B 1/12* (2024.01)
*B08B 7/00* (2006.01)

(52) U.S. Cl.
CPC ...... *A46B 15/0012* (2013.01); *A46B 15/0034* (2013.01); *B08B 1/12* (2024.01); *B08B 7/04* (2013.01)

(58) Field of Classification Search
CPC ........... B08B 1/12; B08B 7/04; B08B 7/0035; A61N 1/0548; A61N 1/40
See application file for complete search history.

(56) References Cited

U.S. PATENT DOCUMENTS

| | | |
|---|---|---|
| 2004/0193235 A1 | 9/2004 | Altshuler et al. |
| 2007/0157404 A1 | 7/2007 | Brewer et al. |
| 2008/0091192 A1 | 4/2008 | Paul et al. |
| 2008/0131834 A1 | 6/2008 | Shepherd et al. |
| 2008/0280248 A1 | 11/2008 | Pitts et al. |
| 2011/0289699 A1 | 12/2011 | Schaefer et al. |
| 2013/0080295 A1 | 3/2013 | Dykes et al. |
| 2015/0157119 A1 | 6/2015 | Barnes et al. |
| 2016/0038762 A1 | 2/2016 | Lin |
| 2018/0255916 A1* | 9/2018 | Levi ..................... A46B 15/004 |
| 2020/0093255 A1 | 3/2020 | Mediratta et al. |

FOREIGN PATENT DOCUMENTS

| | | |
|---|---|---|
| WO | 2013042307 A1 | 3/2013 |
| WO | 2015083155 A1 | 6/2015 |
| WO | 2017216606 A1 | 12/2017 |
| WO | 2021239549 A1 | 12/2021 |
| WO | 2021239553 A1 | 12/2021 |
| WO | 2021239554 A1 | 12/2021 |
| WO | 2021239556 A1 | 12/2021 |

OTHER PUBLICATIONS

ToothWave—Way Beyond Brushing. Silk'n Australia Youtube Video https://www.youtube.com/watch?v=orTsVwZLC10 Mar. 18, 2019.
Halterman. "Researchers Create Stunning 3D Printed, Programmable, Bio-Inspired Architectural Materials", Dec. 11, 2014, 3dprint.com, https://3dprint.com/30045/bio-architectural-materials/.

* cited by examiner

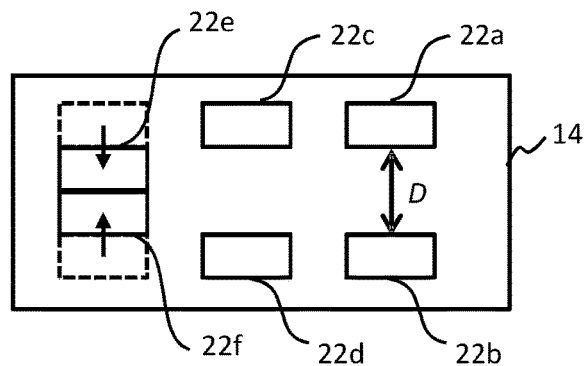
FIG. 5
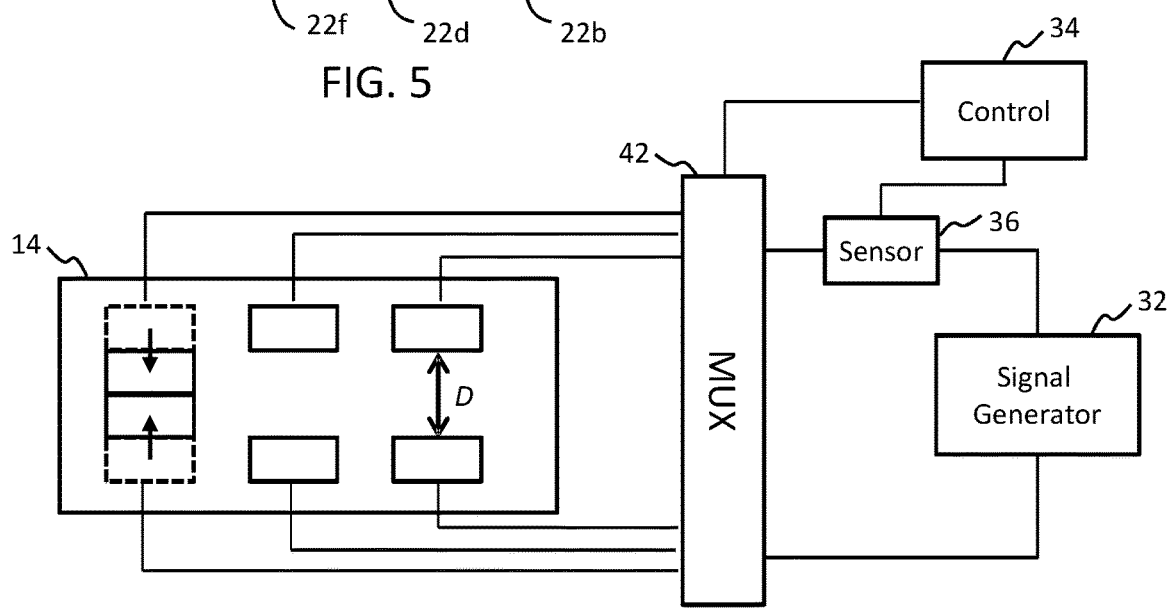
FIG. 6
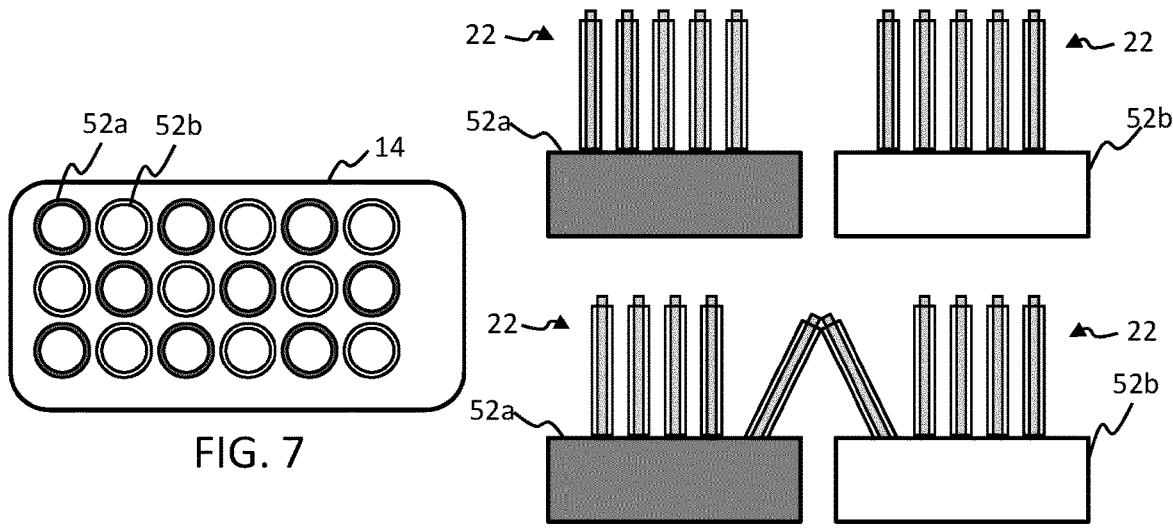
FIG. 7
FIG. 8

PERSONAL CARE DEVICE

This application is the U.S. National Phase application under 35 U.S.C. § 371 of International Application No. PCT/EP2021/082361, filed on Nov. 19, 2021, which claims the benefit of EP Application Serial No. 20216418.2, filed Dec. 22, 2020. These applications are hereby incorporated by reference herein.

FIELD OF THE INVENTION

The present invention relates to a personal care device, in particular a device with RF functionality for a cleaning and/or treatment function.

BACKGROUND OF THE INVENTION

WO-A1-2017/216606 discloses an oral cleaning device that includes a head portion that supports cleaning elements, a handle portion extending from the head portion, and an RF generator disposed in the handle portion, connected to electrodes located on the head portion.

In the field of personal care, a range of devices generate electromagnetic emissions for a personal care function.

One example is oral healthcare. A recent development in the oral healthcare field are oral care devices that generate radio frequency (RF) electromagnetic emissions for an oral cleaning and/or treatment function. Herein, radio frequency (RF) is the oscillation rate of an alternating electric current or voltage or of a magnetic, electric or electromagnetic field or mechanical system in the frequency range from 3 kHz to 30 GHz, so from very low frequencies (VLF) through super high frequencies (SHF) as defined in ITU recommendation ITU-R V.431-8.

Radio frequency (RF) electromagnetic emissions can be used to provide a cleaning function in the oral cavity. In particular, when the RF field interacts with surfaces of the teeth and gums, it may change surface properties of surfaces in the mouth which may soften surface deposits such as plaque or dental calculus, allowing them to be removed more easily. The RF emissions may also provide a treatment function through inducing a mild heating action in tissue.

With constant daily use, components can become worn or degraded, diminishing their operational integrity.

In the field of personal care, replacement of operational parts, such as brush heads, is currently based on a predetermined usage time, or based on counting a number of uses of the device. However, wear-out is highly individual, and can vary between users. Therefore, measuring real wear over time would be highly valuable.

SUMMARY OF THE INVENTION

The invention is defined by the independent claims. The dependent claims define advantageous embodiments.

According to examples of the invention, there is provided a personal care device, comprising an RF signal generator adapted to generate one or more RF drive signals for use during operation in driving a plurality of RF electrodes in accordance with a drive scheme, e.g. for stimulating generation of RF electromagnetic emissions or currents from the RF electrodes. A controller is adapted to detect a degraded functional state of the RF electrodes by monitoring one or more electrical characteristics of the generator circuit during operation, the one or more electrical characteristics being related to a functional status of the RF electrodes; comparing the electrical characteristics with one or more pre-determined criteria; and triggering a response action dependent upon the electrical characteristics meeting the one or more pre-determined criteria.

Embodiments of the invention are based on monitoring a functional status of the RF electrodes by monitoring changes in one or more electrical characteristics of the generator circuit. The functional status can for example relate to a physical status of the RF electrodes (e.g. their physical integrity, their structural shape or degradation thereof), and/or to an electrical functional status, e.g. integrity of signal transmission, or wiring integrity. An aim is to detect a degraded functional state (malfunction, wear-out state) of the RF electrodes.

The controller may be adapted to detect a particular target functional status, and wherein the criteria are configured to correlate with or be indicative of occurrence of that target functional status.

For example, as the RF electrodes become worn, they may bend and splay, which changes a relative spatial positioning of the RF electrodes of any given pair when at rest, which thereby changes electrical properties of RF drive signals within the RF drive circuit (e.g. impedance, current, voltage). Thus, changes in electrical characteristics of the drive circuit (e.g. from a baseline or reference level) can be used to indicate such a change in the physical status of the RF electrodes, which may necessitate replacement of the cleaning and/or treatment unit. It may additionally or alternatively be used to trigger corrective action to circumvent or accommodate possible short-circuiting which may occur as a result of the wear and the changed physical status.

In the context of this disclosure, personal care may refer to personal care of a human or animal.

In the context of this disclosure, being related to a functional status means that the one or more electrical characteristics vary in dependence upon a functional status of the RF electrodes. As the functional status changes, the one or more electrical characteristics that are monitored change. As mentioned above, a functional status may for example relate to a physical status of the RF electrodes and/or to an electrical functionality of the RF electrodes.

The pre-determined criteria are related to or indicative of a certain target function status, i.e. one whose occurrence is sought to be detected. The target functional status is preferably a diminished or degraded functional status compared with a new or factory state, i.e. a malfunction status.

The pre-determined criteria correspond to expected levels or properties of the measured electrical characteristics in the event of a particular target functional status occurring. The criteria are configured to be indicative of a target functional status, in particular a degraded or diminished functional status, e.g. a malfunction or partial or complete wear-out.

The controller may be adapted to detect a wear-out state of the RF electrodes.

In the context of this disclosure, a 'wear-out state', or a 'degraded functional status' means a state of disrepair, or a state of physical or functional degradation. It includes component failure or component malfunction, but also includes a partial wear-out state in which the component repair state is degraded compared to a new state, but has not yet failed. It includes for example any of component failure, component malfunction (including short-circuits) and (persistent or permanent) mechanical deformation or deflection of the RF electrodes. Hence a 'wear-out state' or 'degraded functional status' is intended to cover any state of partial or complete wear-out or deterioration.

In the context of this disclosure, 'RF emissions' may refer to a static or time-varying electric or electromagnetic field, and/or to propagating electromagnetic waves.

The personal care device may comprise a base unit which is adapted to couple during operation with a removable cleaning and/or treatment unit. The provided device may comprise just the base unit, or may comprise the base unit in combination with the cleaning and/or treatment unit. In further examples, the personal care device may comprise the base unit fixedly attached to a cleaning and/or treatment unit.

The personal care device may be an oral care device, for example a toothbrush or a brushing mouthpiece device. The cleaning and/or treatment unit may for example be a head for a toothbrush. Other examples will be discussed later.

In some embodiments, the pre-determined criteria may be configured to be indicative of occurrence of a short circuit between at least two RF electrodes of the plurality of RF electrodes.

As the RF electrodes become worn, they can become physically deformed, so that they may bend toward one another, which leads to a risk of short-circuiting due to contact between the RF electrodes. Short circuiting is a safety hazard due to the excess heat generated, and also due to high intensity RF fields generated if any two RF electrodes are close together.

Detecting the short circuit allows a user to be alerted and/or for remedial action to be taken to avoid safety risks.

It is also possible to predict degradation of functional status based on for instance a trend in the electrical characteristics over time (e.g. over multiple operation sessions) toward a state which would correspond to a pre-determined degraded functional status.

The pre-determined criteria may include a change in the one or more electrical characteristics of the generator circuit during a single operation session of the generator circuit, the change exceeding a threshold magnitude or a threshold rate of change.

A sudden change, or a fluctuation, in an electrical characteristic such as impedance or current may indicate a short-circuit has occurred. It can also indicate other forms of wear or degradation of functional status—for instance a break or fracture of the RF electrode, or deformation in the form of twisting, bending or other physical distortion. Thus, changes in the electrical characteristics can occur due to effects which are localized to a single RF electrode and not necessarily in interaction with another RF electrode.

A single operation session means for example a single continuous active period of the device, e.g. a single continuous active period of the RF signal generator (a period in which the RF signal generator is activated and generating RF drive signals).

The pre-determined criteria may include meeting or passing a threshold value for at least one of the one or more electrical characteristics.

Here, determination of a target (diminished) functional status may be based on long-term drift of an electrical characteristic away from a baseline level, which may for instance be a factory-set level, or a level which is set in a calibration operation performed when the cleaning and/or treatment unit is first used.

The response action may comprise generating a data output indicative of the meeting of the pre-determined criteria (i.e. the detection of the target functional status). This may be for communicating to an external device, such as an external computing device, e.g. a personal computing device, e.g. a smartphone.

The response action may comprise generating a sensory output for altering a user. The sensory output may provide an indication of the functional status change to a user. This may for example indicate a need to replace the cleaning and/or treatment unit, or a portion thereof which comprises the degraded RF electrodes.

In accordance with one or more embodiments, the one or more response actions may include changing the drive scheme of the RF electrodes.

The changing the drive scheme may include selectively deactivating at least one RF electrode of the plurality of RF electrodes.

RF electrodes can be selectively deactivated to avert possible short circuits, or to prevent further short-circuiting where this has already occurred. This thereby allows the device to continue to be used safely for a short period even after wear-out is detected. The wear of the RF electrodes is accommodated, and the device can continue to be used in a temporary wear-out or accommodation mode, with hazardous RF electrodes operationally neutralized.

In accordance with one or more embodiments, the device may further comprise: a cleaning and/or treatment unit comprising a plurality of RF electrodes outwardly extending from a surface of the cleaning and/or treatment unit, and wherein the RF signal generator is arranged for supplying the RF drive signals to the plurality of RF electrodes of the cleaning and/or treatment unit.

The personal care device may comprise a base portion which houses the RF signal generator and controller and wherein the cleaning and/or treatment unit is fixedly or removably coupled to the base portion. The cleaning and/or treatment unit may form a removable attachment to the base unit.

In accordance with one or more embodiments, the cleaning and/or treatment unit may comprise a plurality of cleaning elements which outwardly protrude from the surface of the cleaning and/or treatment unit for engaging with oral surfaces for a cleaning function. The cleaning elements may be for example cleaning filaments or any other type of protruding mechanical cleaning element.

In accordance with one or more embodiments, the cleaning and/or treatment unit may comprise one or more spatial groups of cleaning filaments extending outwardly from the surface of the cleaning and/or treatment unit, each spatial group covering an area of the surface, and wherein each of the RF electrodes is located extending from one of the areas covered by the one or more spatial groups of filaments. A group means a group of two or more. Although cleaning filaments are referred to, these may be any type of mechanical cleaning element which protrudes from the surface of the cleaning and/or treatment unit.

If the RF electrodes are provided as flexible RF electrodes with similar flexibility characteristics as any cleaning filaments comprised by the cleaning and/or treatment unit, then detected functional status of the RF electrodes can provide an indirect indicator of physical functional status of these cleaning filaments, or general wear of the cleaning and/or treatment unit. Degradation of the RF electrodes can effectively provide a proxy measure of the wear of the cleaning filaments and the overall cleaning and/or treatment unit, potentially indicating a need for replacement.

By providing the RF electrodes integrated within the tufts, or fields, of filaments (e.g. bristles), this means that the physical functional status of the RF electrodes (e.g. bending and splaying) can be expected to mirror the physical status of the filaments. Thus short-circuiting, or other changes in the electrical characteristics due to general wear of the RF electrodes, may provide an indication of a general wear-out of the cleaning filaments.

In accordance with one or more embodiments, cleaning and/or treatment unit may comprises a plurality of spatial groups of RF electrodes, each of the spatial groups being individually addressable by the RF signal generator, and wherein the response action comprises selectively activating or deactivating different of the spatial groups of RF electrodes.

The spatial groups may each comprise at least two RF electrodes. The spatial groups may be arranged adjacent, contiguous and/or interleaved with one another. For example, there may be a plurality of rows or lines of RF electrodes adjacent to and/or contiguous with one another. There may be interdigitated rows or groups of RF electrodes. There may be concentrically arranged rings of RF electrodes. Where a short circuit is detected within one spatial group of RF electrodes, that spatial group alone may be deactivated. Where a short circuit is detected between two neighboring spatial groups, one of those spatial groups alone may be deactivated.

In accordance with one or more embodiments, the device may further comprise a pressure sensor arranged to sense a pressure exerted at the cleaning and/or treatment unit, and wherein the triggering of the response action is further based on one or more pre-determined criteria related to an output signal from the pressure sensor.

Here, brushing pressure can be used in combination with the electrical properties of the RF signal generator circuit. In particular, the aim is to determine degradation of functional status (e.g. physical or electrical wear or deformation) of RF electrodes in their natural, rest state, when no external force is being exerted upon them. Thus, for example, the target functional status may be determined based on electrical characteristics of the RF signal generator circuit when the detected pressure is below a defined threshold, for example the threshold indicative of absence of external pressure on the RF electrodes.

In accordance with one or more embodiments, each RF electrode may comprise a conductive element, and wherein each RF electrode comprises a heat-activated element arranged in thermal communication with at least a portion of the conductive element, and adapted to perform a response action upon heat-activation.

The heat-activated element may be a heat-activated end-of life indicator. It may be a heat-activated safety mechanism.

The heat-activated element preferably is a passive heat-activation element, i.e. it comprises a passive heat-activation mechanism. It may comprise a heat-responsive material such as a heat-responsive smart material.

The heat-activated element is adapted to trigger responsive to the heat generated by a short circuit, caused by contact between exposed portions of two RF electrodes.

In some examples, at least a portion of the conductive element may be arranged to be exposed and wherein the heat-activated element is arranged in thermal communication with the exposed portion.

'Exposed' in this context means that the relevant portion of the conductive element is open to, or in direction fluid communication with, the environment surrounding the cleaning and/or treatment unit, e.g. the environment of the oral cavity when received therein. This allows for efficient output of RF energy or currents from the electrode.

The exposed portion of the conductive element may be a distal or tip portion, extending from a terminal distal point of the conductive element to a more proximal point. Proximal in this disclosure means closer to a surface of the cleaning and/or treatment unit, and distal means further from a surface of the cleaning and/or treatment unit.

The heat-activated element is provided in addition to the electrical functional status monitoring discussed above.

The heat-activated element may be adapted to provide a visual indication upon heat-activation. Here, the heat-activated element may provide a visual wear-out indicator.

Additionally or alternatively, the heat-activated element may be adapted to exhibit a mechanical response action upon the heat-activation.

As mentioned, at least a portion of the conductive element may be arranged to be exposed and wherein the heat-activated element is arranged in thermal communication with the exposed portion. In some examples, the heat-activated element may be adapted to transition from a first physical configuration to a second physical configuration upon heat-activation, and wherein, in the second physical configuration, the heat-activated element covers the exposed portion of the conductive element.

In the first configuration, the exposed portion is not covered. In the second configuration, the exposed portion is no longer exposed. By covering the exposed portion of the conductive element when deformation or deflection and consequent short-circuit is detected (via the heat-activation), this prevents further contact between the exposed portion and other RF electrode conductive elements, and thus prevents further short-circuiting.

Thus, this allows the device to continue to be safely used for a short period even after a short-circuit is detected. In effect, this embodiment puts the device into an end-of-life usage mode in which short-circuiting RF electrodes are neutralized.

In accordance with one or more further embodiments, the heat-activated element may be adapted to transition from a first physical configuration to a second physical configuration upon heat-activation, and wherein, in at least one of the physical configurations, the element is arranged to be within an electromagnetic field, or an electromagnetic emission output path, of the RF electrode during operation, and wherein the controller is adapted to detect a change in the signal characteristics of the RF generator circuit caused by the change in the physical configuration of the heat-activated element.

Here the movement of the indicator within the field of the RF emissions, due to the heat-activated triggering, causes a change in signal characteristics of the RF generator circuit and thus provides a way to detect the change in functional status electronically via the passive activation of the wear-out indicator.

In accordance with one or more embodiments, each RF electrode may comprise a conductive element covered by a sheath.

In some examples, a distal portion of the sheath may be adapted to release from the RF electrode upon fracturing of a join between the distal and proximal portions, to thereby expose a distal region of the conductive element, wherein the join is adapted to fracture following a pre-determined amount of strain.

In this embodiment, the conductive element is designed to be covered by an insulating sheath in a normal operation state of the device. After a pre-determined amount of wear, a distal section of the sheath is adapted to release to expose an end of the conductive element. As a result, this provides a visual indicator of end-of life, thus allowing the end of life wear to be detected. It also may change the electrical characteristics of the generator circuit due to the physical alteration to the sheath, which provides an electrically detectable indicator of end of life.

Further examples of the invention provide a method comprising controlling an RF signal generator of a personal care device to generate one or more RF drive signals for driving a plurality of RF electrodes in accordance with a drive scheme (e.g. to thereby stimulate generation of RF electromagnetic emissions or currents from the RF electrodes); and detecting a degraded functional state of the RF electrodes by monitoring one or more electrical characteristics of the RF signal generator, the electrical characteristics being related to a functional status of the RF electrodes;
comparing the electrical characteristics with one or more pre-determined criteria; and
triggering a response action dependent upon the electrical characteristics meeting the one or more pre-determined criteria.

Examples in accordance with a further aspect of the invention provide a computer program product comprising computer program code configured, when executed on a processor, to cause the processor to perform a method in accordance with any example or embodiment outlined above or described below, or in accordance with any claim of this application.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 5 and FIG. 6 illustrate selective deactivation of RF electrodes based on detection of wear or failure;

FIG. 7 and FIG. 8 illustrate a device having spatial groups of RF electrodes, and selective deactivation of spatial groups based on detection of wear or failure of an RF electrode in the group;

DETAILED DESCRIPTION OF THE EMBODIMENTS

Figure 1:
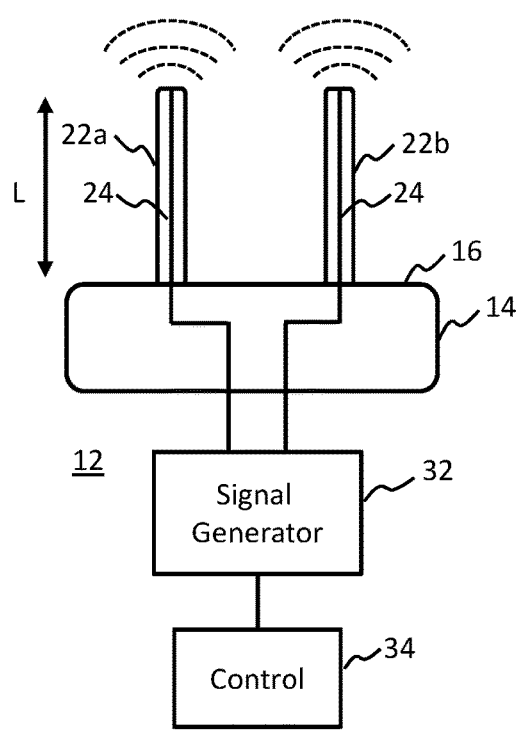
FIG. 1 and FIG. 2 show components of an example device in accordance with one or more embodiments.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a personal care device comprising functionality for generating RF-frequency electromagnetic emissions or currents for a cleaning or treatment function. The RF emissions or currents may be output from a set of two or more RF electrodes (e.g. electrodes) upon stimulation with an RF drive signal from an RF signal generator. The device further includes a controller for monitoring a functional status of the RF electrodes via monitoring changes or variations in one or more electrical characteristics of the RF signal generator circuit, e.g. drift in one or more electrical characteristics from reference factory levels, or sudden changes in the characteristics, indicating a short-circuit. A response action can be generated based on the electrical characteristics meeting pre-defined criteria indicative of a particular (e.g. degraded) functional status, for example generating a sensory alert for a user or data output, or performing remedial action such as deactivating sensed defective or worn electrodes.

In some embodiments, the response action may comprise switching the device to a dedicated wear-out or malfunction accommodation mode in which degraded or defective RF electrodes are deactivated, or a control scheme of the elements is adjusted to minimize impact on device functionality or to avoid safety hazards. Additionally or alternatively, the response action may comprise providing a sensory indicator to a user, i.e. with a sensory output.

The functional status monitored by the device may for example relate to a physical status of the RF electrodes (e.g. their physical integrity, their structural shape or degradation thereof), and/or to an electrical functional status, e.g. integrity of signal transmission, wiring integrity. An aim is to detect a degraded or diminished functional status or condition, e.g. a malfunction or degraded functional state. The degraded functional status can include for example physical degradation, such as persistent physical deformation of RF electrodes, and also electrical failure or malfunction, such as broken or defective conductive elements or wiring. The degraded functional status may correspond to a wear-out state, which may be a full wear out state (component failure) and/or a partial wear-out state, in which the RF electrode is degraded, but has not yet failed or malfunctioned.

FIG. 1 shows components of an example personal care device 12 in accordance with one or more embodiments.

The device 12 comprises an RF signal generator 32 arranged for supplying during operation one or more RF drive signals to a plurality of RF electrodes 22 in accordance with a drive scheme, e.g. for stimulating generation of RF emissions or currents from the RF electrodes. The RF emissions may include a time-varying electric or electromagnetic field, and/or they may include propagating RF-frequency electromagnetic waves.

The device 12 may additionally comprise a cleaning and/or treatment unit 14 comprising the plurality of RF electrodes 22 outwardly extending from a surface 16 of the cleaning and/or treatment unit. Two RF electrodes 22a, 22b are shown in FIG. 1, but more may typically be provided. The cleaning and/or treatment unit may, by way of non-limiting example, be a brush head for a toothbrush, a mouthpiece portion of a brushing mouthpiece device, or a head section of a skin brushing device.

The device 12 further comprises a controller 34, operatively coupled to the RF signal generator 32.

The controller 34 is adapted to monitor one or more electrical characteristics of the generator circuit during operation. The one or more electrical characteristics are related to a functional status of the RF electrodes. The controller is further adapted to assess the electrical characteristics with one or more pre-determined criteria. The controller is further adapted to trigger a response action dependent upon the electrical characteristics meeting the one or more pre-determined criteria.

The one or more pre-determined criteria are configured or set so as to correspond to a particular target functional status, i.e. one whose occurrence is sought to be detected. The target functional status is preferably a diminished or degraded functional status, i.e. a malfunction status.

The controller is further adapted to trigger a response action dependent on the meeting of the criteria, i.e. dependent upon detection of the target functional status.

In further embodiments, the cleaning and/or treatment unit may be omitted from the provided device. Instead the device may comprise the RF signal generator circuit and controller without the cleaning and/or treatment unit, and wherein the RF signal generator is adapted to electrically couple to the plurality of RF electrodes for stimulating generation of RF emissions. For example, the device may comprise a base unit housing the RF signal generator and the controller, and which is adapted to couple to the cleaning and/or treatment unit.

The 'generator circuit' means for example a circuit which comprises the RF signal generator 32 and at least one RF electrode 22 electrically coupled to the generator, for example at least one pair of RF electrodes. The device may comprise a plurality of generator circuits, each comprising the, or a, RF signal generator in combination with one or more RF electrodes.

Figure 2:
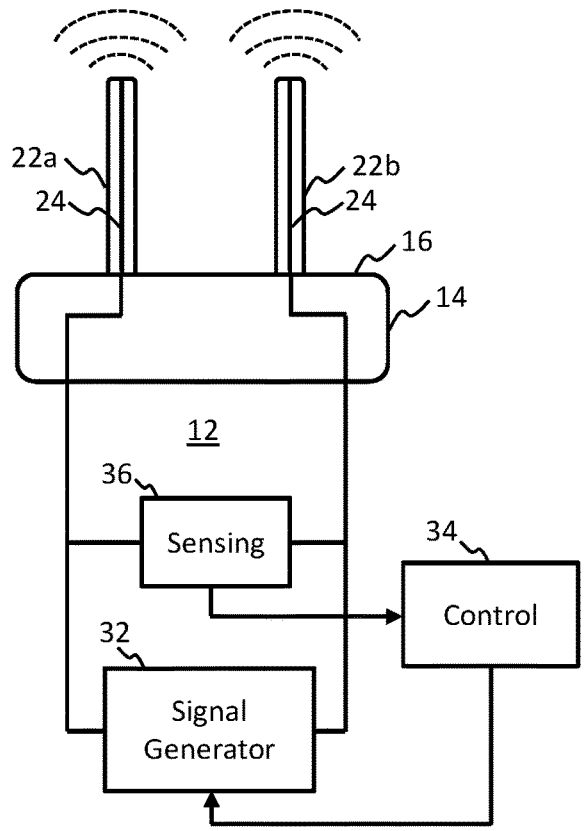

As illustrated in FIG. 2, in some examples, the device 12 may further include a sensor module 36 electrically coupled with the RF signal generator 32 for sensing one or more electrical characteristics of the circuit between the RF signal generator 32 and the RF electrodes 22. The controller 34 may receive an output signal from the sensor module 36 and may be adapted to monitor the functional status, i.e. assess the pre-determined criteria, based on this output signal.

The RF electrodes 22 may each include a conductive element 24 electrically coupled to the RF signal generator. The conductive element may be at least partially covered by an insulating sheath. By way of non-limiting example, the RF electrodes may comprise electrodes (e.g. conductive plates, e.g. flexible metal electrode strips (lamellae), wires, or coils).

The RF electrodes 22 are preferably flexible in a lateral direction, meaning a direction perpendicular a direction of their length, L, extending from a proximal end, where the RF electrode makes contact with the surface 16 to a distal tip of the RF electrode. This is advantageous for instance for cases in which the device is for a cleaning function and includes flexible cleaning elements (e.g. bristles) protruding from the same surface 16 of the cleaning and/or treatment unit. This is because the RF electrodes can bend along with the flexible cleaning elements, which improves usability and cleaning functionality.

The RF signal generator 32 may be an oscillator. It may be adapted to generate an RF drive signal in the form of an alternating current or voltage.

Although radio frequency drive signals are specifically mentioned above, the RF signal generator may be adapted to generate drive signals for stimulating electromagnetic emissions in the radio frequency or microwave frequency bands, for example between 3 kHz and 30 GHz, or more preferably between 100 kHz and 30 GHz.

The plurality of RF electrodes 22 may include a plurality of pairs of electrodes and wherein RF electrodes of each pair are driven with differing voltages, or with reciprocally alternating voltages, to induce a time-varying potential difference between the pair. Each pair may be separately and individually controllable. However, this drive configuration is not essential. In some examples, the plurality of RF electrodes may comprise a plurality of subsets of RF electrodes, each subset being individually controllable. In further examples, individual RF electrodes may be separately controllable.

The controller 34 is adapted to monitor one or more electrical characteristics of the RF signal generator circuit. These may include for example, impedance, current, or voltage.

The controller is adapted to apply or assess one or more pre-determined detection criteria related to the monitored one or more electrical characteristics. The device may further include a local memory or datastore in which the criteria are recorded and wherein the controller 34 is adapted in operation to retrieve the criteria. In further examples, the criteria may be implicitly provided in one or more detection algorithms with which the controller is programmed, or which the controller is adapted to execute. The criteria may include a threshold, or a specified range, for values of one or more of the electrical characteristics. The criteria may include a threshold or specified range for a rate of change of one or more of the electrical characteristics. The criteria may include a threshold or specified range for a deviation or change in one or more of the electrical characteristics from a reference value (e.g. a factory default value).

For any of the above, instead of the criteria being related directly to the electrical characteristics, they may relate to secondary properties or values derived from the electrical characteristics, e.g. signal waveform features or frequency/spectral properties related to the circuit electrical characteristics.

There are a number of different possible applications for the embodiments of the invention. The device 12 is generally applicable within the field of personal care devices, particularly handheld personal care devices. One advantageous field of application is oral care devices (e.g. a powered toothbrush or a powered mouthpiece device), and various embodiments discussed below will be described in relation to an oral care device. However, in each case, it is to be understood that the technical features contributing to the technical effect of the embodiment may be applied equally to personal care devices in different fields such as hair brushes, skin brushes, massage brushes, foot brushes, face brushes, and beard brushes. Furthermore, embodiments of the invention are not only suitable for human personal care, but also for animal (e.g. pet) care. By way of example, the provided personal care device may be a pet oral care device, or a pet brushing device.

Advantages of the proposed device are that changes in functional status of the RF electrodes can be detected using integral components of the device itself, without need to incorporate additional dedicated detection or monitoring components.

Example features according to one or more example embodiments will now be outlined in more detail.

In operation, RF electrodes 22 of the device 12 may become physically worn or deformed. For example, in some embodiments, the device may be an oral care device which includes protruding flexible cleaning filaments or elements for physically engaging with oral surfaces. In this context, the RF electrodes may be frequently knocked or bent, leading to degradation over time. For example, the RF electrodes may be included among the bristle field of an oral care device. The RF electrodes themselves may be flexible, and thus liable to be bent toward one another in the course of normal operation. This is most likely to happen for example at moments when the device is (temporarily) removed from dental surfaces (e.g. to move it to a different part of the mouth), but can also happen during teeth cleaning. Over time, the RF electrodes may become permanently or persistently bent toward one another.

Figure 3:
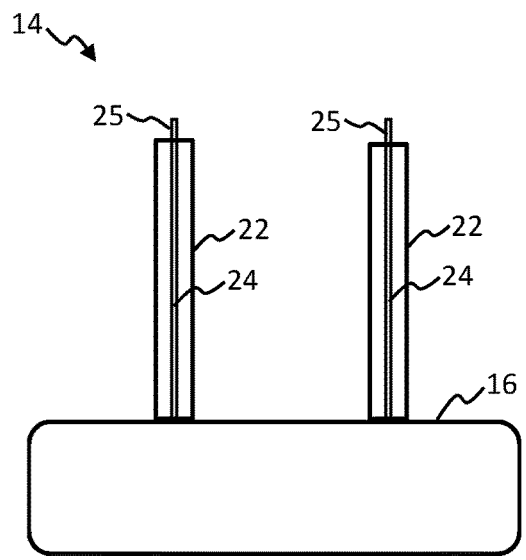
FIG. 3 and FIG. 4 schematically illustrate physical deformation of RF electrodes leading to contact and short-circuiting.
Figure 4:
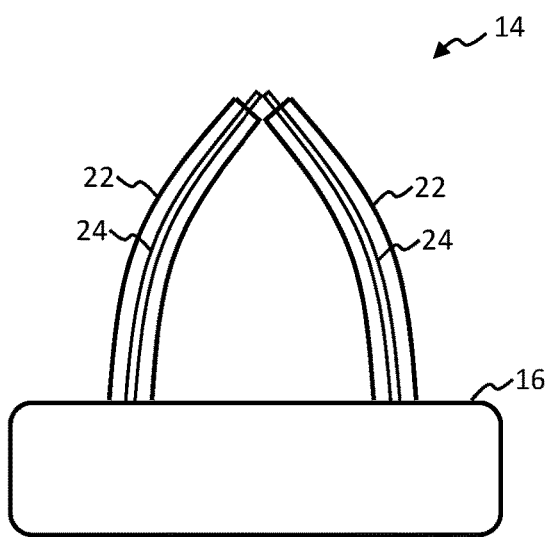

This is illustrated schematically in FIG. 3 and FIG. 4. FIG. 3 shows an example cleaning and/or treatment unit 14 having RF electrodes 22 in a non-degraded functional status, in which the RF electrodes 22 are straight. A non-degraded functional status might in further examples have the elements at a different pre-determined arrangement, for example tilted and/or twisted relative to the surface 16. FIG. 4 shows the cleaning and/or treatment unit 14 in a degraded functional status state, in which the RF electrodes of FIG. 3 have become permanently bent toward one another. Here, the degradation of functional status corresponds a degradation of physical status. The electrical status may also be degraded due to the deformation.

Exposed sections 25 of the conductive elements 24 comprised by the RF electrodes may come into contact. This may lead to short-circuiting, which can lead to electrical malfunction and also poses a safety hazard due to the heat generated and possible sparking. The deformation of elements by itself is also an undesirable condition since it leads to diminished performance, and the short circuit can also simply be used as an indicator of this undesirable state of wear. If the RF electrodes are nestled within a field of cleaning filaments, physical deformation of the cleaning filaments over time can also induce deformation in the RF electrodes, due to pressing of the cleaning filaments onto the RF electrodes.

Thus, according to one or more embodiments, short-circuiting may be utilized as an indicator of degraded functional status, i.e. as a wear-out or end of life indicator. The controller may thus be adapted to monitor the electrical characteristics to detect a short circuit between at least two RF electrodes 22 of the plurality of RF electrodes. Thus, the pre-determined criteria may be configured to be indicative of occurrence of a short circuit between at least two RF electrodes of the plurality of RF electrodes.

By way of example, in this case, the pre-determined detection criteria may include a change in the one or more electrical characteristics of the generator circuit during a single operation session of the generator circuit, the change exceeding a threshold magnitude or a threshold rate of change.

A single operation session means for example a single continuous active period of the device, e.g. a single continuous active period of the RF signal generator (a period in which the RF signal generator is activated and generating RF drive signals).

Occurrence of a short circuit may lead to a sudden large increase in electrical characteristics such as current, voltage or impedance in the generator circuit. This can be detected as a threshold change in the value of the electrical characteristic or a threshold rate of change.

In advance of a level of deterioration which leads to short-circuiting, the RF electrodes 22 may enter a state of partially degraded functional status (partial wear-out state) in which they are partially bent toward one another. In other words, a distance between the RF electrodes may change from a first distance to a second, smaller distance. This may be detectable as a threshold change in one or more electrical characteristics from a reference or baseline level, where the reference or baseline level corresponds to the level when the device is in a zero-wear state, i.e. optimal functional status, or from a calibration level (e.g. when the cleaning and/or treatment unit is first used). The reference or baseline level may be stored in a local datastore or memory for example, for reference by the controller 34.

The electrical characteristic may be impedance for example. Drift in the generator circuit impedance over multiple operation sessions may indicate change in the distance between the RF electrodes 22 comprised in that generator circuit.

In some examples, the one or more predetermined criteria may include detection of the threshold change in the one or more signal characteristics when the device is in a rest state or inactive state (i.e. indicating a persistent or permanent physical deformation).

FIG. 5 and FIG. 6 schematically illustrate detection of degraded functional status of RF electrodes of an example cleaning and/or treatment unit 14 comprising a plurality of RF electrodes 22. As shown in FIG. 6, the RF electrodes in this example are controlled as a set of three pairs of RF electrodes: a first pair 22a, 22b, second pair 22c, 22d and a third pair 22e, 22f. Each of the pairs can be independently controlled, and the electrical characteristics of each independently sensed, by means of an analog multiplexer ('MUX') 42. Each pair of RF electrodes is electrically coupled to the multiplexer. The controller 34 is operatively coupled to the multiplexer for controlling the signals supplied to each RF electrode pair. The RF signal generator 32 is arranged to supply an RF drive signal to the multiplexer, and wherein the supply of this signal to each of the pairs can be selectively activated or deactivated by the multiplexer according to control signals from the controller 34. A sensor module 36 is adapted to monitor signal characteristics of the generator circuit branch to each of the pairs of RF electrodes, and is arranged to feed this information to the controller.

In a zero-wear state of undiminished functional status, each pair of RF electrodes 22 is separated by a distance, D. As the unit 14 is used, and becomes worn, RF electrodes 22 of one or more of the pairs 22e, 22f may bend toward one another, as illustrated in FIG. 5 and FIG. 6 in relation to pair 22e, 22f. This may lead to a change in the electrical characteristics, such as (capacitive) impedance, which is detectable by the sensor unit 36, and in turn by the controller 34. If the change exceeds a pre-determined threshold, corrective action may be taken, for example deactivating the pair of RF electrodes which have deflected toward one another. This avoids the possibility of short-circuiting in the event that the RF electrodes come into contact with one another.

Thus, in other words, the signal characteristics, such as measured (capacitive) impedance, are used to sense a change in the distance D between one or more pairs of RF electrodes, and responsive to detecting a change exceeding a threshold, the controller 34 may control selective deactivation of the respective pair of electrodes which exceeds the threshold separation distance change.

Likewise, if a short-circuit is detected in a particular pair of RF electrodes, that pair may be selectively deactivated.

Thus, in these examples the response action triggered by the controller comprises a change to the drive scheme of the RF electrodes.

Although FIG. 5 and FIG. 6 comprise pairs of RF electrodes 22 which are independently controllable, instead the device may include subsets of RF electrodes of more than two which are independently controllable. All of the features described above for the pairs of RF electrodes can be applied equally in the case of subsets larger than two.

Based on detection that the one or more pre-determined criteria have been met (indicative of a certain functional status of the RF electrodes 22 occurring, e.g. reduction of a separation distance between RF electrodes or short-circuiting of RF electrodes), a response action is triggered by the controller 34. The response action may comprise generating alerts to inform a user of the determined functional status change, and/or may comprise corrective action (such as deactivating selected RF electrodes, as discussed above).

In some examples, the response action comprises generating a sensory output for communicating the detection to a user. For example, the device may comprise one or more controllable lighting elements, e.g. LEDs, which are controlled by the controller to illuminate in the event of the criteria being met. Further examples may include means for generating an acoustic output, or to generate haptic feedback for alerting the user.

In accordance with one or more embodiments, the plurality of RF electrodes 22 comprised by the device 12 may be arranged in a plurality of spatial groups or subsets on the surface 16 of the cleaning and/or treatment unit 14. The different spatial groups or subsets may be spaced from one another on the surface 16 of the cleaning and/or treatment unit 14. Each of the spatial groups may be individually addressable by the RF signal generator 32. In some examples, the response action of the controller when the pre-determined criteria are met may comprise selectively activating or deactivating different of the spatial groups of RF electrodes. For example, if signal characteristics detected in a particular one of the spatial groups of RF electrodes indicate a degraded functional status of an RF electrode in that spatial group, the spatial group may be selectively deactivated to avoid short-circuits and device malfunction.

One example is schematically illustrated in FIG. 7 and FIG. 8. In this example, the plurality of spatial groups comprises non-overlapping annular arrangements 52a, 52b of RF electrodes 22. The annular arrangements may be incorporated or mixed within an outer annular region of a tuft of cleaning elements such as bristles. Each annular arrangement of RF electrodes is electrically supplied via a separate conductive track set into a base structure which surrounds the arrangement. This base structure (e.g. a ring) may also serve to hold together a tuft of cleaning elements.

FIG. 8 schematically illustrates an example of adjacent annular arrangements 52a, 52b of RF electrodes 22 in a non-degraded (top) and degraded (bottom) functional status respectively. In the degraded state, the RF electrodes of adjacent groups may come into contact. In this case, at least one of the spatial groups may be deactivated by the controller 34 to avoid short-circuiting.

Additionally or alternatively, independently controllable spatial groups of RF electrodes 22 can be provided having different geometries.

Figure 9:
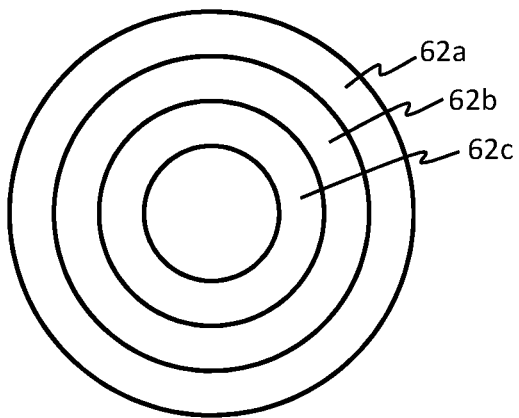
FIGS. 9-11 show different example geometric arrangements for spatial groups of RF electrodes.

One example is illustrated in FIG. 9. This example comprises concentric annular rings 62a, 62b, 62c of RF electrodes.

Figure 10:
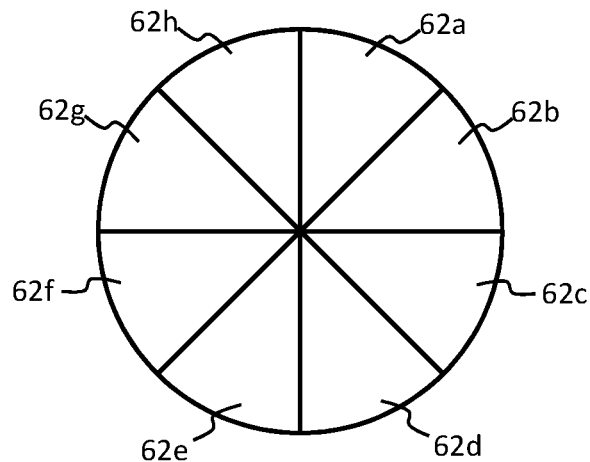

Another example is illustrated in FIG. 10. This example comprises radially segmented spatial groups of RF electrodes, i.e. the spatial groups comprise segments 62a-62h of a circle or of the interior of any closed curve shape.

Figure 11:
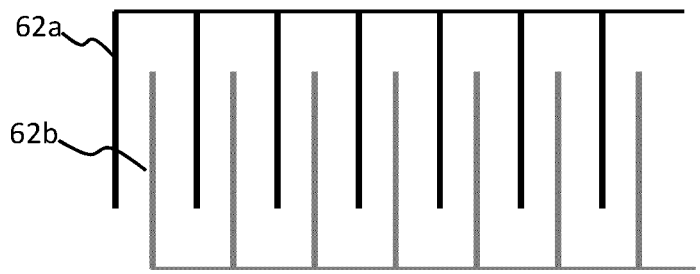

Another example is illustrated in FIG. 11. This comprises interdigitated lines 62a, 62b of RF electrodes.

These represent just one selection of example geometries. Any other example geometry may also be contemplated, for example circular or oval spatial groups (i.e. a solid circle or oval, rather than just an annulus), square spatial groups, triangular spatial groups, rectangular spatial groups, parallelogram spatial groups or diamond-shaped spatial groups.

In each example, the spatial group 62 of RF electrodes may be supplied by a conductive track, plate or pattern or tracks which extends across the area covered by the spatial group, to permit all RF electrodes located in the respective group to be electrically driven with a common RF drive signal. This allows for independent control of each of the different spatial groups by changing the RF drive signal which is supplied to the conductive tracks or plate corresponding to each spatial group; e.g. can be deactivated or activated or supplied with different electrical RF drive signals (e.g. different frequency) based on the measured functional status.

As mentioned above, one or more of the spatial groups of RF electrodes 22 may coincide with a group of cleaning elements or filaments, such a tuft of bristles. For example, the cleaning and/or treatment unit 14 may comprise one or more spatial groups of cleaning filaments extending outwardly from the surface 16 of the cleaning and/or treatment unit 14, each spatial group covering an area of the surface, and wherein each of the RF electrodes 22 is located extending from one of the areas covered by the one or more spatial groups of filaments.

This enables control of RF fields within a particular group (e.g. tuft or bundle) of cleaning filaments, and/or between groups.

In accordance with one or more embodiments, the pre-determined criteria applied by the controller may be configured to correspond to, or be indicative of, a pre-determined lateral deflection (distance) of an RF electrode. In other words, they correspond to a target degraded functional status in which the RF electrode is physically deformed with a determined lateral deflection. Lateral means in a direction perpendicular a direction of the length of the RF electrode. A pre-determined lateral deflection means a deflection (bending) of the RF electrode in this direction so that its distal end (e.g. tip) is a certain pre-determined lateral distance from its proximal-most point (where it meets the surface 16 of the cleaning and/or treatment unit 14).

In accordance with one or more embodiments, the spacing between neighboring spatial groups of the cleaning filaments may be configured to be less than or equal to double this pre-determined lateral deflection distance, and wherein RF electrodes are provided extending from locations of the surface 16 at an outer periphery of each spatial group. This has the effect that as soon as the RF electrodes comprised in both neighboring spatial groups have reached the pre-determined amount of lateral deflection (i.e. target degraded function status, or wear-out state, has been reached), contact between exposed distal portions of the conductive elements 24 of each RF electrode are likely to come into contact, causing a short-circuit which can then be detected by the controller as explained above.

In some embodiments, the spacing between the neighboring spatial groups of the cleaning filaments may be configured to be less than or equal to the pre-determined lateral deflection distance (i.e. not double the distance). This has the effect that if the RF electrodes of only one of the spatial groups reaches the pre-determined deflection, then the short circuit becomes likely and the functional status change can be detected. The RF electrodes located in neighboring spatial groups of cleaning filaments may be driven with differing, e.g. opposite, voltages so that contact leads to short circuit.

In accordance with one or more embodiments, the device may include means for changing a physical configuration of the RF electrodes, and wherein the response action implemented by the controller comprises controlling a change in the physical configuration. This can be for the purpose of providing a visual indication to a user of the detected functional status change. It may additionally or alternatively be for the purpose of forcing a permanent end-of-life state of the RF electrodes. For example, there may be means for stimulating deflection of two RF electrodes of a pair toward one another until they contact, leading to short-circuit and permanent end-of life. This may be triggered responsive to detecting a target functional status change of one or both of the RF electrodes, e.g. due to a detected short circuit. This then avoids future malfunction and short circuits caused by the elements.

To implement the controlled change of distance between the RF electrodes 22, there may be provided an actuation element at a base of at least a subset of the RF electrodes which permits adjustment of an angle of the element relative to the surface 16 of the cleaning and or/treatment unit 14. For example, this may comprise an actively controllable swivel joint. It may comprise an electroactive material actuator which can expand responsive to electrical stimulation to thereby manipulate the orientation of the RF electrode.

In some embodiments, the personal care device may further comprise a pressure sensor arranged to sense a pressure exerted at one or more locations of the cleaning and/or treatment unit 14, and wherein the triggering of the response action is further based on one or more pre-determined criteria related to an output signal from the pressure sensor.

This may permit discrimination between transient RF electrode contact (and consequent short-circuit) caused by normal movement of the RF electrodes 22 during use, and persistent deformation of the RF electrodes. For example, in the case of an oral care device, during normal use, the RF electrodes may be knocked by bristles flexing as a result of contact with teeth, e.g. when tufts are splayed because of brushing pressure. Temporary contact between RF electrodes in this state does not necessarily indicate a degraded functional status. Thus, the response action may in some examples only be triggered in the event that the pressure signal is below a pre-defined threshold, and the electrical characteristics meet the pre-defined criteria for these characteristics. This ensures that the relevant electrical characteristic criteria are occurring in a static or idle state of the device (low or no pressure applied to the surface 16 of the cleaning and/or treatment unit 14).

In some examples, short circuiting events and detected pressure may be tracked concurrently over time by the controller 34 and a combination of both used to determine a changing functional status of the device 12 over time.

The pressure sensor may be incorporated in a handle or base portion of the personal care device. It may detect a pressure exerted on the cleaning and/or treatment unit relative to the base unit. For example, the base unit may be adapted to physically couple with the cleaning and/or treatment unit via a coupling arm, and wherein a pressure exerted on the mechanical coupling arm by the cleaning and/or treatment unit is detected.

In accordance with one or more embodiments, the device may further comprise a passive heat-activated element carried by each RF electrode 22 and arranged to be exposed to the heat generated upon contact and short-circuiting between two RF electrodes. For example, each RF electrode 22 may comprise a conductive element 24, and wherein at least a portion of the conductive element is exposed 25. Contact between RF electrodes leading to short circuit may occur between the exposed portions 25. Each RF electrode 22 may comprise a passive heat-activated element arranged in thermal communication with the exposed portion, and adapted to perform a response action upon heat-activation.

Figures 12, 13:
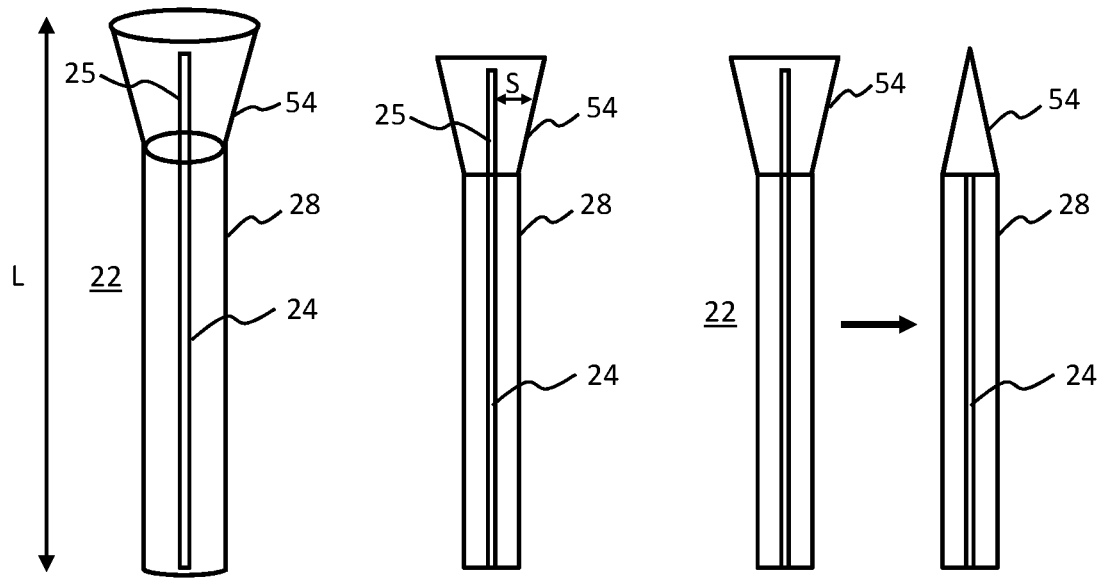
FIG. 12 shows an example RF electrode having a physical shield element configured to shield against contact between RF electrodes.
FIG. 13 shows an example RF electrode having a heat-responsive wear indicator adapted to be triggered based on heat generated by a short-circuit.

An example is illustrated in FIG. 12 and FIG. 13. In this example, the heat-activated element 54 takes the form of an annular element arranged to surround the exposed portion 25 of the conductive element 24. In particular, the heat activated element 54 comprises a wall which is spaced from the exposed portion 25 of the conductive element. However, these structural details are not essential.

Because the heat-activated element 54 surrounds the exposed portion 25 of the conductive element 24, it becomes exposed to heat generated if the exposed portion contacts the conductive element 24 of another RF electrode, triggering heat-activation.

The heat activated response action may provide a visual indication to a user. For example, the element may change shape. The heat-activated element may be adapted to exhibit a mechanical response action upon heat-activation.

In some examples, the heat-activated element 54 may be adapted to transition from a first physical configuration to a second physical configuration upon heat-activation.

In some examples, in the second physical configuration, the heat-activated element may cover the exposed portion 25 of the conductive element. This example is illustrated in FIG. 13, where FIG. 13 (left) shows the RF electrode 22 and the heat-responsive element 54 before heat-activation, and FIG. 13 (right) shows the RF electrode and heat-responsive element after heat-activation. In this example the element 54 changes from a shape having an open face at a distal end (cup-shaped) to a shape which is closed at the distal end. This closing of the element protects the exposed portion of the conductive element from further contact with other RF electrodes, thus avoiding further short circuiting. The closing can also provide a visual indicator to a user of an end-of-life or wear-out state of the element, which may trigger the user to replace the cleaning and/or treatment portion 14.

In accordance with one or more examples, the heat-activated element 54 may be adapted to transition from a first physical configuration to a second physical configuration upon heat-activation, and wherein, in at least one of the physical configurations, the heat-activated element is arranged to be within an electromagnetic field, or an electromagnetic emission output path, of the RF electrode 22 during operation, and wherein the controller 34 is adapted to detect a change in the signal characteristics of the RF generator circuit caused by the change in the physical configuration of the heat-activated element.

By way of example, for the example heat-activated element 54 of FIG. 13, the closure of the element may additionally lead to a change in detectable electrical characteristics of the generator circuit.

In a further example, the heat-activated element 54 may be adapted to separate from the RF electrode 22 upon heat-activation. This would provide both a visual and electrically detectable indicator of wear-out or failure of the RF electrode. For example, the element 54 shown in FIG. 12 might in a further example be adapted to release from the RF electrode upon heat activation. This would change properties of the electromagnetic field surrounding the RF electrode which in turn would lead to a detectable change in electrical characteristics. It would also provide a visual indication of end-of-life.

Figure 14:
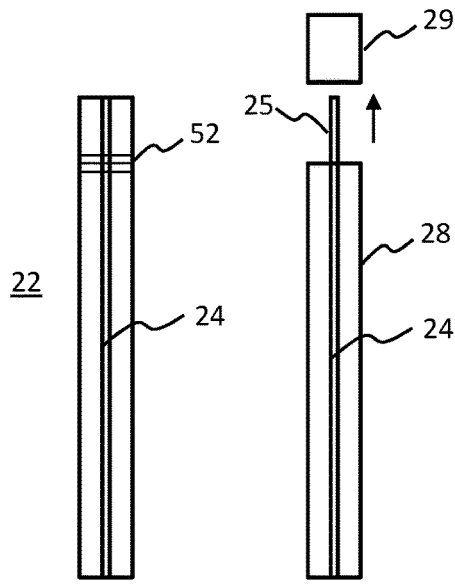
FIG. 14 shows an RF electrode having a physical end-of-life indicator adapted to be released after a threshold amount of physical stress.

A further example is illustrated in FIG. 14. In this example, each RF electrode 22 comprises a conductive element 24 covered by an insulating sheath 28. As depicted in FIG. 14 (right), a distal portion 29 of the sheath is adapted to release from the RF electrode upon fracturing of a (sacrificial) join 52 between the distal and proximal portions, to thereby expose a distal region 25 of the conductive element 25, wherein the join is adapted to fracture following a pre-determined amount of strain.

This thus provides a purely passive material-inherent solution. The RF electrode is provided having a predetermined breaking point which is configured to fail under shear stress or torsion/torque as a consequence of repeated mechanical cycle stresses exerted during normal use. It can be designed in such a way that it breaks or starts breaking after a pre-determined amount of time, e.g. after 2-3 months of use, or after a pre-determined amount of use.

Figure 15:
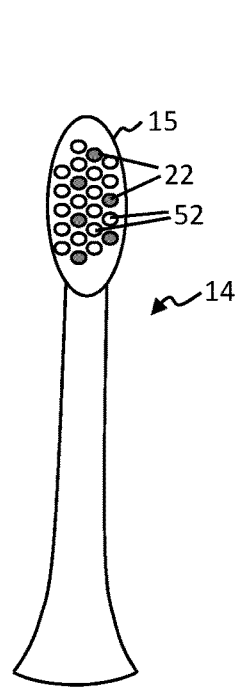
FIGS. 15-16 show an example oral care device in the form of a toothbrush, in accordance with one or more embodiments.
Figure 16:
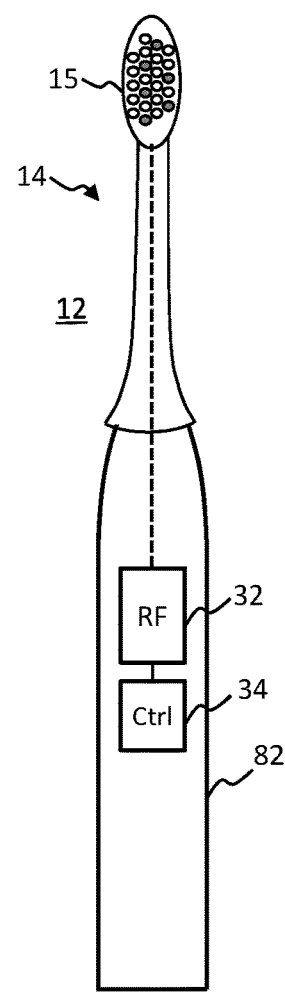

FIGS. 15-16 illustrate one example oral care device 70 in the form of a toothbrush. In this example, the cleaning and/or treatment unit 14 is in the form of a detachable brush head for the toothbrush, and wherein the RF electrodes 22 and also a bristle field 52 is carried on a surface of a platen 15 of the brush head. The brush head in this example forms a removable attachment to a base portion 82 of the toothbrush, the base portion forming a handle for the device. The RF signal generator 32 and controller 34 are housed within the base portion 82.

The provided oral care device according to the invention may comprise just the base portion 82 of the device illustrated in FIGS. 15-16, which is adapted to couple the cleaning and/or treatment unit 14 during operation. Alternatively, it may comprise the base portion in combination with the cleaning and/or treatment unit 14.

In preferred embodiments, the oral care device 12 further comprises a mechanical movement generator (not shown) arranged to apply an oscillatory movement to the brush head. This may be coupled to the controller 34. The oscillatory movement causes oscillation of the cleaning filaments (bristles) which enhances cleaning action when the cleaning filaments are applied against oral surfaces. It may also enhance any treatment action provided by the RF electrodes 22 when operational.

The oscillatory movement generator may be provided housed in the base portion 82, and arranged to apply the oscillatory movement to the cleaning and/or treatment unit 14.

The base unit 82 and the cleaning and/or treatment unit 14 may comprise complementary electrical connectors arranged such that, upon mechanical coupling or docking of the cleaning unit 12 to the base unit, electrical connection is established between the RF signal generator 32 and the RF electrodes 22 comprised by the cleaning unit.

Although the example of FIGS. 15-16 shows an oral care device 70 in the form of a toothbrush, this is not essential. By way of further non-limiting example, the oral care device may take the form of a brushing mouthpiece device, comprising a body (e.g. U-shaped, J-shaped or C-shaped) defining tooth-receiving channels, and with bristles arranged protruding into the channels for a tooth cleaning function. Further examples include oral irrigators, powered flossing devices or any other oral care device.

Figure 17:
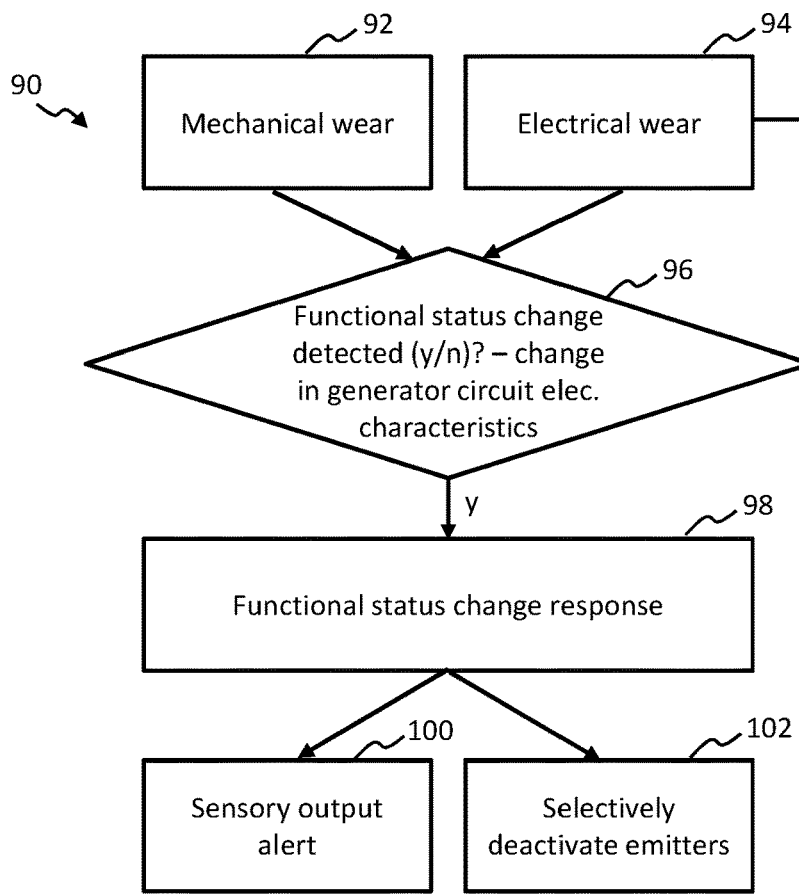
FIG. 17 outlines steps of an example operational workflow according to one or more embodiments.

FIG. 17 briefly summaries the operational workflow 90 of example embodiments of the invention. Embodiments aim to detect mechanical wear or degradation 92 and/or electrical wear or degradation 94 of the cleaning and/or treatment unit 14 or components thereof. The controller 34, based on monitoring electrical characteristics of the generator circuit, and applying one or more pre-determined criteria, detects 96 occurrence of a target functional status change, e.g. a degraded functional status. If the target functional status change is detected, a response 98 is triggered. The response may comprise alerting 100 a user, e.g. with a sensory output. The response may additionally or alternatively comprise selectively deactivating 102 RF electrodes which are detected to have the functional status change.

Examples in accordance with a further aspect of the invention provide a method, comprising:
controlling an RF signal generator of a personal care device to generate one or more radio frequency (RF) drive signals for driving a plurality of RF electrodes in accordance with a drive scheme e.g. to thereby stimulate generation of RF electromagnetic emissions or currents from the RF electrodes;
monitoring one or more electrical characteristics of the RF signal generator, the electrical characteristics being related to a functional status of the RF electrodes;
comparing the electrical characteristics with one or more pre-determined criteria; and
triggering a response action dependent upon the electrical characteristics meeting the one or more pre-determined criteria.

Examples in accordance with a further aspect of the invention provide a processor configured to perform the method as set out above, or in accordance with any embodiment or claim of this application.

Examples in accordance with a further aspect of the invention provide a computer program product comprising computer program code configured, when executed on a processor, to cause the processor to perform a method in accordance with any example or embodiment outlined above or described below, or in accordance with any claim of this application.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. Measures recited in mutually different dependent claims can advantageously be combined. If the term "adapted to" is used in the claims or description, it is noted the term "adapted to" is intended to be equivalent to the term "configured to". Any reference signs in the claims should not be construed as limiting the scope.

The invention claimed is:

1. A personal care device, comprising:
   an RF signal generator adapted to generate one or more RF drive signals in a frequency range from 3 kHz to 30 GHz for use during operation in driving a plurality of RF electrodes in accordance with a drive scheme; and
   a controller adapted to detect a degraded functional state of the RF electrodes by
      monitoring one or more electrical characteristics of the RF signal generator during operation, the one or more electrical characteristics being related to a functional status of the RF electrodes;
      comparing the electrical characteristics with one or more pre-determined criteria; and
      triggering a response action dependent upon the electrical characteristics meeting the one or more pre-determined criteria.

2. A personal care device as claimed in claim 1, wherein the criteria are configured to be indicative of occurrence of a short circuit between at least two RF electrodes of the plurality of RF electrodes.

3. A personal care device as claimed in claim 1, wherein the pre-determined criteria include a change in the one or more electrical characteristics of the RF signal generator during a single operation session of the RF signal generator, the change exceeding a threshold magnitude or a threshold rate of change.

4. A personal care device as claimed in claim 1, wherein the pre-determined criteria include a threshold value for at least one of the one or more electrical characteristics.

5. A personal care device as claimed in claim 1, wherein the response action comprises generating a data output, and/or comprises generating a sensory output for alerting a user.

6. A personal care device as claimed in claim 1, wherein the one or more response actions include changing the drive scheme of the RF electrodes; and/or selectively deactivating at least one RF electrode of the plurality of RF electrodes.

7. A personal care device as claimed in claim 1, further comprising:
   a cleaning and/or treatment unit comprising the plurality of RF electrodes outwardly extending from a surface of the cleaning and/or treatment unit, wherein the RF signal generator is arranged for supplying the RF drive signals to the plurality of RF electrodes of the cleaning and/or treatment unit.

8. A personal care device as claimed in claim 7, wherein the cleaning and/or treatment unit comprises one or more spatial groups of cleaning filaments extending outwardly from the surface of the cleaning and/or treatment unit, each spatial group covering an area of the surface, and wherein each of the RF electrodes is located extending from one of the areas covered by the one or more spatial groups of cleaning filaments.

9. A personal care device as claimed in claim 7, wherein the cleaning and/or treatment unit comprises a plurality of spatial groups of RF electrodes, each of the spatial groups being individually addressable by the RF signal generator, and wherein the response action comprises selectively activating or deactivating different of the spatial groups of RF electrodes.

10. A personal care device as claimed in claim 7, wherein the device further comprises a pressure sensor arranged to sense a pressure exerted at the cleaning and/or treatment unit, and wherein the triggering of the response action is further based on one or more pre-determined criteria related to an output signal from the pressure sensor.

11. A personal care device as claimed in claim 7, wherein each RF electrode comprises a conductive element, and wherein each RF electrode comprises a passive heat-activated element arranged in thermal communication with at least a portion of the conductive element, and adapted to perform a response action upon heat-activation.

12. A personal care device as claimed in claim 11, wherein the heat-activated element is adapted to provide a visual indication upon heat-activation; and/or exhibit a mechanical response action upon the heat-activation.

13. A personal care device as claimed in claim 7, wherein at least a portion of the conductive element is exposed and the heat-activated element is arranged in thermal communication with the exposed portion, and wherein the heat-activated element is adapted to transition from a first physical configuration to a second physical configuration upon heat-activation, and wherein, in the second physical configuration, the heat-activated element covers the exposed portion of the conductive element.

14. A computer program product comprising computer program code configured, when executed on a processor, to cause the processor to perform a personal care method comprising:
   controlling an RF signal generator of a personal care device to generate one or more RF drive signals in a frequency range from 3 kHz to 30 GHz for driving a plurality of RF electrodes in accordance with a drive scheme;
   detecting a degraded functional state of the RF electrodes by
      monitoring one or more electrical characteristics of the signal generator, the electrical characteristics being related to a functional status of the RF electrodes;
      comparing the electrical characteristics with one or more pre-determined criteria; and
   triggering a response action dependent upon the electrical characteristics meeting the one or more pre-determined criteria.

* * * * *